United States Patent
Kerr et al.

(10) Patent No.: US 9,918,768 B2
(45) Date of Patent: Mar. 20, 2018

(54) METHOD FOR AUGMENTING, REDUCING, AND REPAIRING BONE WITH THERMOPLASTIC MATERIALS

(75) Inventors: Sean H. Kerr, Oreland, PA (US); Ali Cem Recber, Piscataway, NJ (US)

(73) Assignee: DEPUY SYNTHES PRODUCTS, INC., Raynham, MA (US)

(*) Notice: Subject to any disclaimer, the term of this patent is extended or adjusted under 35 U.S.C. 154(b) by 349 days.

(21) Appl. No.: 13/613,629

(22) Filed: Sep. 13, 2012

(65) Prior Publication Data
US 2013/0023879 A1    Jan. 24, 2013

Related U.S. Application Data

(63) Continuation of application No. 11/801,779, filed on May 10, 2007, now abandoned.
(Continued)

(51) Int. Cl.
| | |
|---|---|
| *A61B 17/68* | (2006.01) |
| *A61B 17/84* | (2006.01) |
| *A61B 17/88* | (2006.01) |
| *A61B 17/70* | (2006.01) |
| *A61K 9/00* | (2006.01) |
| *A61B 17/16* | (2006.01) |

(52) U.S. Cl.
CPC .......... *A61B 17/8855* (2013.01); *A61B 17/68* (2013.01); *A61B 17/7097* (2013.01); *A61B 17/7098* (2013.01); *A61B 17/84* (2013.01); *A61K 9/0024* (2013.01); *A61B 17/1615* (2013.01); *A61B 17/686* (2013.01); *A61B 17/8805* (2013.01)

(58) Field of Classification Search
CPC ....................................................... A61L 2/081
USPC ................. 606/76–78, 92–94, 300, 301, 304
See application file for complete search history.

(56) References Cited

U.S. PATENT DOCUMENTS

| | | | | |
|---|---|---|---|---|
| 4,200,939 A | * | 5/1980 | Oser | ............................... 606/76 |
| 4,494,535 A | | 1/1985 | Haig | |

(Continued)

FOREIGN PATENT DOCUMENTS

WO        02/34310 A2        2/2002

OTHER PUBLICATIONS

Yasuda Norihiko, Compound Composition and Thermally Recoverable Article (JPS5911315 (A), Jan. 20, 1984.*
Abstract of JPS5911315 (A).*

*Primary Examiner* — Nicholas Woodall
(74) *Attorney, Agent, or Firm* — Fay Kaplun & Marcin, LLP

(57) ABSTRACT

A method for augmenting a tissue including introducing into the tissue a first thermoplastic material at a first condition; treating the first thermoplastic material to achieve a second condition that includes an at least partially crystalline skin; and introducing a second material into the tissue whereby the first thermoplastic material and the second material are contained by the at least partially crystalline skin. Also a method of fracture reduction in a tissue including exposing to gamma radiation a mass of polycaprolactone characterized by a first shape; heating the mass of irradiated polycaprolactone above its melting temperature; introducing the heated mass of polycaprolactone into the tissue annulus to deform it from the first shape; allowing the material to return to the first shape.

7 Claims, 7 Drawing Sheets

Related U.S. Application Data

(60) Provisional application No. 60/799,283, filed on May 10, 2006.

(56) References Cited

U.S. PATENT DOCUMENTS

| | | | |
|---|---|---|---|
| 4,645,503 A | 2/1987 | Lin et al. | |
| 5,043,396 A * | 8/1991 | Kitahara et al. | 525/332.9 |
| 5,679,723 A | 10/1997 | Cooper et al. | |
| 5,709,548 A * | 1/1998 | Oxman | A61C 9/0006 433/218 |
| 5,741,256 A | 4/1998 | Bresina | |
| 5,749,922 A * | 5/1998 | Slepian et al. | 29/469.5 |
| 6,165,486 A * | 12/2000 | Marra et al. | 424/423 |
| 6,290,982 B1 | 9/2001 | Seppala et al. | |
| 6,402,757 B1 | 6/2002 | Moore et al. | |
| 6,517,542 B1 | 2/2003 | Papay et al. | |
| 6,599,448 B1 * | 7/2003 | Ehrhard et al. | 252/582 |
| 6,620,185 B1 | 9/2003 | Harvie et al. | |
| 6,793,660 B2 | 9/2004 | Kerr et al. | |
| 6,818,001 B2 | 11/2004 | Wulfman et al. | |
| 6,835,197 B2 | 12/2004 | Roth et al. | |
| 7,144,414 B2 | 12/2006 | Harvie et al. | |
| 7,250,055 B1 * | 7/2007 | Vanderwalle | 606/92 |
| 8,221,477 B2 * | 7/2012 | Aeschlimann et al. | 606/300 |
| 2002/0099385 A1 | 7/2002 | Ralph et al. | |
| 2002/0193883 A1 | 12/2002 | Wironen | |
| 2004/0049194 A1 * | 3/2004 | Harvie et al. | 606/72 |
| 2004/0068261 A1 | 4/2004 | Fourcault et al. | |
| 2004/0093014 A1 * | 5/2004 | Ho et al. | 606/200 |
| 2004/0267265 A1 | 12/2004 | Kyle | |
| 2005/0080423 A1 | 4/2005 | Hagan et al. | |
| 2005/0209629 A1 | 9/2005 | Kerr et al. | |
| 2005/0249697 A1 * | 11/2005 | Uhrich | A61K 9/1647 424/78.37 |
| 2006/0241604 A1 | 10/2006 | Frigg et al. | |
| 2007/0244550 A1 | 10/2007 | Eidenschink | |
| 2007/0260250 A1 * | 11/2007 | Wisnewski et al. | 606/73 |
| 2008/0167658 A1 * | 7/2008 | Kerr et al. | 606/93 |

\* cited by examiner

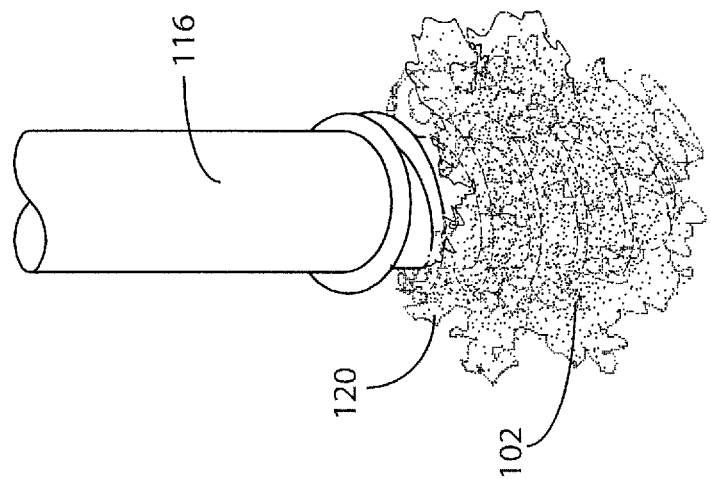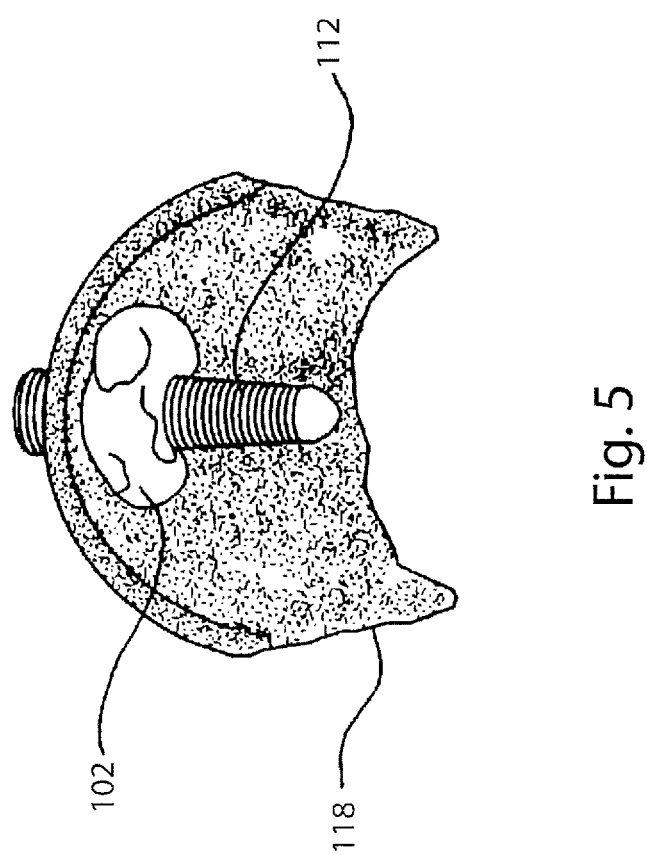

METHOD FOR AUGMENTING, REDUCING, AND REPAIRING BONE WITH THERMOPLASTIC MATERIALS

CROSS REFERENCE TO RELATED APPLICATION

This application is based off and claims priority to U.S. patent application Ser. No. 11/801,779, filed May 10, 2007, which claims priority to U.S. Provisional Patent application No. 60/799,283, filed May 10, 2006, the content of both applications is hereby incorporated herein by reference in their entirety.

INCORPORATION BY REFERENCE

Each and every reference cited herein is hereby incorporated by reference as if set forth in its entirety herein.

TECHNICAL FIELD OF THE INVENTION

Generally, the present invention relates to methods and materials for augmenting and repairing bone.

BACKGROUND OF THE FIELD OF THE INVENTION

Current standards for attaching implants such as plates to bones often constitute screws in a plurality of shapes. The purpose of these screws is to transfer the load from one bone fragment to the plate or nail and back to a secondary bone fragment.

To ensure this load transfer, the screws must have a good connection in the bone and the plate. The connection between the plate and the screw can be achieved with an angular stable system, which transfers the load through a form-fitted connection, not through friction between the plate and screw. Recent advancements in locked plating systems have enabled the clinician to easily achieve this angular stable construct in normal healthy bone.

However, even angular stable constructs fail in osteoporotic bone because of a lack of stability in the bone to screw interface. Osteoporosis is characterized by a reduction of bone mass and also by alteration in the architecture of the bone. The trabecular bone structure is changing significantly. These changes are taking place after the 6th decade of life and women are more affected than men. The whole skeleton is affected by osteoporosis, with varying amount of impact throughout the body. The regions most severely affected by osteoporosis are the spine, proximal femur, distal radius, proximal humerus and proximal tibia. Treating osteoporotic fractures in these areas can be very challenging for the surgeon because the screws can not find sufficient purchase in the weak trabecular structure. There is at times a complete absence of bone where the surgeon would normally place the screw, such as in the proximal humerus.

One method of improving the fixation between the screw and the osteoporotic bone has been to augment the bone with a hardenable biomaterial such as PMMA cement or calcium phosphate (CaP) cement. Each of these methods has disadvantages.

For example, disadvantages of using PMMA include the permanent non-resorbing nature of PMMA. It remains within the body after the fracture has healed and removal of the material is nearly impossible once implanted. The stiffness of PMMA is in excess of the surrounding bone creating excess stress at the interface to the bone. PMMA can release monomer during the curing process and the monomer can become vascularized. PMMA releases noxious fumes during the mixing and curing process requiring special ventilation. PMMA is initially too runny to handle and can quickly become too difficult to implant and the state of the material is not reversible. PMMA has a minimal ductility, can bind to metals making screw removal difficult, and can be difficult to control the direction of implantation. PMMA can either extravasate into the canal of the diaphysis (rendering it ineffective), into the joint space or become vascularized (leading to an embolism). Furthermore, PMMA includes a risk of thermal necrosis due to the exothermic reaction during curing.

There has been recent interest in using calcium phosphate cements for augmentation of screws and other fracture fixation devices. Calcium phosphate will slowly remodel over time and does not contain a monomer, however, it has the following deficiencies. The stiffness of calcium phosphate is in excess of the surrounding bone creating excess stress at the interface to the bone. Calcium phosphate will inherently not perfuse into surrounding bone without the addition of a flow enhancing agent. Calcium phosphates are subject to phase separation if they are overpressurized. Calcium phosphate includes a variable time and temperature dependent rheology. The calcium phosphate materials will not properly set unless the surrounding tissue is near 37° C. It can be difficult to control the direction of implantation of calcium phosphates and calcium phosphates can either extravasate into the canal of the diaphysis (rendering it ineffective), into the joint space or become vascularized (leading to an embolism). Calcium phosphates include suboptimal mechanical properties while they often have adequate compressive strength, they have little tensile strength, flexural strength or ductility. Furthermore, additional calcium phosphate material will not bond to calcium phosphate material that has already set and the drillability and screwability of the calcium phosphate is limited.

Improvements have been made to calcium phosphate cements such as adding reinforcing fibers and flow enhancing agents. The addition of reinforcing fibers actually renders the cement less advantageous for hardware augmentation since the fiber will be filtered by the trabecular structure surrounding the hardware and will impede perfusion. Flow enhancing agents such as hyaluronic acid will improve some of the handling properties of the calcium phosphate cements and will allow perfusion. However the material remains suboptimal for the application.

There also exists a need for improved materials when no fixation hardware is used. Such instances would include augmenting osteoporotic bone such as a vertebral body or to fill voids where the bone has been compressed due to trauma. The purpose of the material in this case is not to fixate the hardware to the bone, but rather to directly replace or augment the bone. PMMA is commonly used for vertebroplasty procedures but suffers from many of the problems stated above. Calcium phosphate cements can be used as well, but also with the above limitations. Further, in these types of applications there often exists a need to reduce the fractures or to compress the surrounding bone, which the existing materials are not capable of doing.

SUMMARY OF THE INVENTION

The present invention relates to a method for augmenting a tissue including the steps of introducing into the tissue a first thermoplastic material at a first condition; treating the first thermoplastic material to achieve a second condition that includes an at least partially crystalline skin; and introducing a second material into the tissue such that the first thermoplastic material and the second material are contained by the at least partially crystalline skin.

In some embodiments, the introduction of the second material causes the at least partially crystalline skin to expand. In some embodiments, the at least partially crystalline skin is forced against at least a portion of the tissue in response to the introduction of second material into the first thermoplastic material. This step of forcing the at least partially crystalline skin against at least a portion of the tissue may include displacing at least a portion of the tissue. In some embodiments, at least a portion of the first thermoplastic material surrounds at least a portion of the second material.

In some embodiments the second material is thermoplastic material. In certain embodiments, the first thermoplastic material and the second material are the same thermoplastic material. In some embodiments, at least one of either the first thermoplastic material or the second material is polycaprolactone. In certain embodiments, at least one of either the first thermoplastic material or the second material is an at least partially crystalline polymer. In other embodiments, the first thermoplastic material or the second material is a substantially crystalline polymer. In certain embodiments, the second material is osteosynthesis hardware. In some embodiments, at least a third material is introduced into the tissue.

In some embodiments, the tissue is bone, such as cancellous bone which is compressed when the crystalline skin expands. In other embodiments, the tissue is mobile bone fragments, which are reduced when the crystalline skin expands. In some embodiments, the tissue is a collapsed vertebral body, the height of which is increased when the crystalline skin expands.

In some embodiments, the step of treating the first thermoplastic material includes changing the temperature of the first thermoplastic material. In some embodiments, the step of treating the first thermoplastic material includes cooling the first thermoplastic material. In some embodiments, the first thermoplastic material is treated by inserting a cooling device into the first thermoplastic material. In certain embodiments, the treating step includes allowing the first thermoplastic material to achieve the second condition by exposure to ambient conditions in the tissue. In some embodiments, the second material is introduced when the temperature of the second material is higher than the temperature of the first thermoplastic material. The second material may be introduced into the tissue in a molten state. In certain embodiments, the first thermoplastic material and the second material are cooled after the second material is introduced into the tissue.

In some embodiments, the first condition is a flowable state. In some embodiments, the second condition is a semi-solid state. In various embodiments, at least a portion of the first thermoplastic material is partially crystallized when the first thermoplastic material is at the second condition. In certain embodiments, at least a portion of the first thermoplastic material is in a semi-solid state when the first thermoplastic material is at the second condition, and the second material is introduced into the tissue by injecting the second material into the first thermoplastic material. In some embodiments, the temperature of the first thermoplastic material at the first condition is at or above the melting point of the first thermoplastic material, and the temperature of the first thermoplastic material at the second condition is below the melting point of the first thermoplastic material.

In some embodiments, the first thermoplastic material is injected into the tissue. In some embodiments, the second material is injected into the tissue. In certain embodiments, the second material is introduced into the tissue by injecting at least a portion of the second material into the first thermoplastic material. In various embodiments, the first thermoplastic material is introduced to the tissue by introducing the first thermoplastic material into an annulus defined by the tissue.

In various embodiments, the temperature of at least a portion of the tissue is increased prior to introducing the first thermoplastic material into the tissue. In other embodiments, the temperature of at least a portion of the tissue is decreased prior to introducing the first thermoplastic material into the tissue.

In certain embodiments, the first thermoplastic material and the second material are the same material and the treating step includes interrupting the introduction of the first thermoplastic material to allow the first thermoplastic material to achieve the second condition by exposure to ambient conditions in the tissue before the introduction of the second material. In other embodiments, the first thermoplastic material is irradiated prior to introducing the first thermoplastic material into the tissue. In some embodiments, the first thermoplastic material is exposed to gamma radiation to induce a shape memory characteristic on the first thermoplastic material.

In some embodiments, the first thermoplastic material has a rate of crystallization that is adjusted by combining the first thermoplastic material with a substance having a radiodensity that is greater than the radiodensity of the first thermoplastic material. In some embodiments, the substance includes at least one of a calcium compound, barium sulfate, strontium carbonate, a zirconium compound, a magnesium compound, titanium oxides and compounds, and combinations thereof.

In some embodiments, prior to introducing the first thermoplastic material into the tissue, the degree of discontinuity in the structure of the first thermoplastic material is increased to adjust the rate of crystallization of the first thermoplastic material. In some embodiments, increasing the degree of discontinuity in the structure of the first thermoplastic material includes combining the first thermoplastic material with a radiopacifier.

In one embodiment, a method of fracture reduction in a tissue includes exposing to gamma radiation a mass of polycaprolactone characterized by a first shape; heating the mass of irradiated polycaprolactone above its melting temperature; introducing the heated mass of polycaprolactone into a tissue annulus in a shape deformed from the first shape; and allowing the mass of polycaprolactone to return to a shape that approaches the first shape. In some embodiments, the gamma radiation comprises gamma radiation in the range of about 15 kGy to about 50 kGy. In one embodiment, allowing the mass of polycaprolactone to return to a shape that approaches the first shape includes cooling the mass of polycaprolactone. In one embodiment the cooling includes active cooling. In another embodiment, the cooling includes passive heat dissipation.

In a further embodiment, the first shape of the material includes a substantially tubular configuration having a first diameter and wherein heating the mass of irradiated polycaprolactone above its melting temperature permits the introduction of the mass into an interior aperture of a cannulated device, the interior aperture having a diameter that is smaller than the first diameter.

In some embodiments, a method for augmenting a tissue includes adjusting a rate of crystallization of a thermoplastic material by combining the thermoplastic material with a substance having a radiodensity that is greater than the radiodensity of the thermoplastic material; introducing into the tissue the adjusted thermoplastic material at a first condition; and treating the thermoplastic material to achieve a second condition that includes an at least partially crystalline skin. In some embodiments, the thermoplastic material at least partially includes polycaprolcatone.

BRIEF DESCRIPTION OF THE FIGURES

FIG. 5 shows how the material of the present invention can be used to augment the screw in the intramedullary canal according to an embodiment of the present invention;

FIGS. 6 and 7 show augmentation of a Dynamic Hip Screw (DHS) with the materials of the present invention according to an embodiment of the present invention;

DETAILED DESCRIPTION OF EMBODIMENTS OF THE INVENTION

Figure 2:
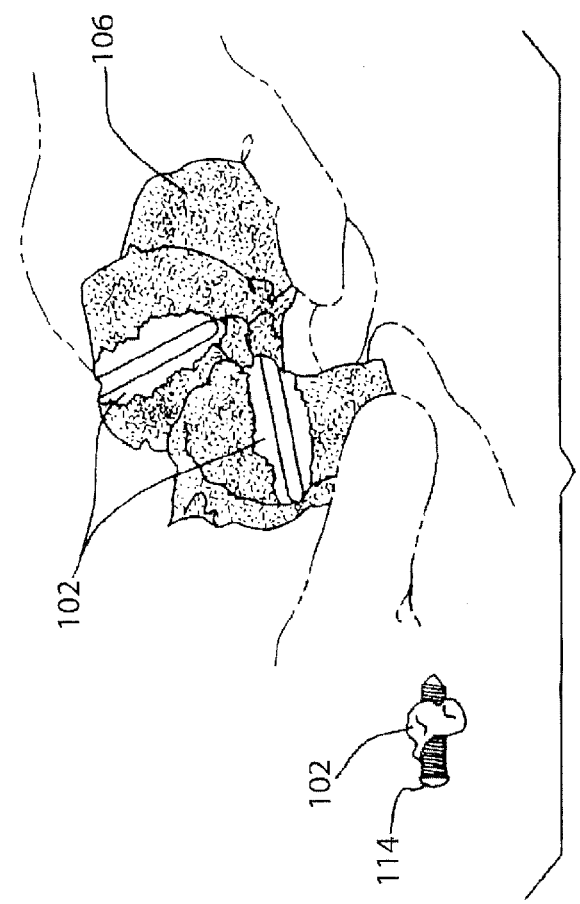
FIGS. 1 and 2 show PCL material injected into a drill hole of a cadaver before placement of a locking screw according to an embodiment of the present invention.

The present invention is generally directed to thermoplastic materials and methods of manipulating thermoplastic materials for the augmentation, reduction, and repair of bone. In some embodiments, the thermoplastic materials of the present invention include crystalline aliphatic polyester polymer. In some embodiments, a preferred thermoplastic material of the present invention include polymers with high molecular weight (Mw), high inherent viscosity (I.V.), crystalline structure, and low melt temperatures. In one embodiment, the thermoplastic polymer includes poly(ε-caprolactone), also known as polycaprolactone or PCL. The preferred grade of PCL has an I.V. of about 1.0 dl/g to about 1.3 dl/g and a molecular weight greater than about 100,000 (Molecular weight and I.V. are generally directly correlated in polymers). In a preferred embodiment, a PCL appropriate for the methods and materials of the present invention is available from and manufactured by Durect Corp. (Pelham, Ala.) and is marketed under the trade name Lactel®. The following are the chemical and physical properties as provided by this manufacturer: Inherent Viscosity (dl/g) between about 1.1 dl/g to about 1.3 dl/g; Melting point, Tm (° C.) between about 58° C. and about 63° C.; Glass Transition, Tg (° C.) between about −65° C. and about −60° C.; Approximate resorption time greater than 2 yrs; Specific Gravity about 1.11; Tensile Strength (MPa) between about 20 MPa and about 35 MPa; Elongation (%) between about 300% and about 500%; and Modulus (MPa) between about 200 MPa and about 350 MPa.

Similar grades of PCL material are available from other sources such as Sigma-Aldrich (St. Louis, Mo.) and others material suppliers. The Lactel® PCL polymer is manufactured under GMP conditions making it suitable for implantation, but otherwise appears equivalent to other available PCL materials of similar Mw. Although PCL is a preferred thermoplastic polymer, the use of other polymers having similar and suitable characteristics is also contemplated for use in the invention.

PCL is a crystalline aliphatic polyester polymer. In one embodiment, the amount of crystallinity of the PCL is approximately 50%. It slowly degrades through hydrolyzation in a manner similar to other aliphatic polyester polymers such as polylactic acid (PLA) and polyglycolic acid (PGA). PCL's resorption time is generally longer, in the order of 2 or more years. The desired grade of PCL is preferably a solid at ambient conditions and physiological conditions with a high degree of toughness, tensile and compressive strength. The modulus of the material is approximately 250 MPa making it similar to the modulus of cancellous bone and an order of magnitude less stiff (lower modulus) than PMMA or calcium phosphate (CaP) cement.

Another unique feature of PCL is that is has a melting point (Tm) of approximately 60° C. The crystalline structure of the material will be lost above 60° C. yielding a viscous fluid that can be manipulated by hand like putty or can be injected. The material can be heated in a variety of commercially available heating devices, such as the Synthes Water Bath (available from Synthes USA, West Chester, Pa.; Part No. 530.510) which heats a sterile tray of water to approximately 70° C. The material can also be heated in a variety of other devices, including but not limited to the Synthes Hot Air system, a chemical heat pack or a heated delivery gun.

In one embodiment, the PCL can be heated with a delivery gun that is capable of holding and delivering the PCL material in an injectable form. A plunger is driven by a device similar to a caulking gun with a spring-loaded squeezable handle assembly, such as Synthes Part No. 353.000. In one exemplary embodiment, a material-holding chamber similar in design to a caulking tube with an outlet or injection nozzle at one end may be approximately 10 mm in diameter and heated by a resistive heater that is externally powered and controlled by a standard process controller with a thermocouple disposed in the material chamber. In one embodiment, the chamber is heated with a resistive material with a positive temperature coefficient (PTC) effect. In such a case the resistance of the heater will increase as the chamber nears the desired temperature and will maintain the appropriate temperature without the addition of a separate temperature controller. The chamber is removeably attached to the gun by mating pairs of flanges on the chamber and gun. Squeezing the handle advances the plunger, which in turn ejects PCL from the chamber nozzle. Injection temperatures of about 80° C. have been found to produce good results; however, other injection temperatures capable of producing satisfactory results may also be used which is also dependent in part on the type of polymer employed.

According to another embodiment of the present invention, an injection device includes a heater powered by internal batteries with an internal temperature controller.

The batteries may be rechargeable in some embodiments. Therefore, the entire device is self-contained thereby eliminating external wires and, thus, the device can be made to be disposable. The material chamber may be elongated or oblong in shape in some embodiments and include an injection nozzle on one end. An end of the chamber may be removeably attached to the Synthes gun (Part No. 353.000) discussed above. The chamber may be connected to the gun via mating flanges on both the chamber and gun which may be rotated circumferentially into and out of engagement. The chamber may include a moveable wall which is engaged by the plunger of the gun and moved axially to expel PCL or another thermoplastic material. In some embodiments, the chamber may be made of injection molded plastic suitable for use in a clinical environment. The self-contained injection device may include an on/off switch, adjustable or non-adjustable temperature regulator to vary the temperature of the material and its viscosity and working time, and various status indicators such as LED's to indicate such parameters as "power on," "ready" when the material has reached the desired delivery temperature for injection, or other parameters of interest. In some embodiments, an LCD or other display may be provided to show the actual temperature of the device, power on, ready status, etc.

In some embodiments, the injection device may have a dual chamber. In one embodiment, the dual chamber is contained within a single external shell. In another embodiment, each chamber is contained within a separate shell. In one embodiment, one chamber may contain the PCL or similar thermoplastic and the other chamber may contain a bioactive or therapeutic agent such as, but not limited to, an antibiotic, growth factor, analgesic, or other similar or dissimilar therapeutic agents. The injection device can be a two-piece or a one-piece device. In one embodiment, the two-piece device includes a chamber and a gun. In other embodiments, the heated chamber may be incorporated in an axial screw-type and/or plunger device such as the syringe disclosed in U.S. Pat. No. 6,793,660, incorporated herein by reference in its entirety.

In some embodiments, the nozzle is elongated and temperature controlled to control the thermodynamic state of the material as it is being injected. In one embodiment the nozzle is actively cooled to reduce the temperature of the ejected material to decrease working time, promote crystallization and/or reduce the risk of thermal necrosis. In one embodiment, the nozzle is actively heated to increase the working time of the material, retard the rate of crystallization and/or to remelt the material if it has prematurely hardened in the nozzle. The means of actively heating the nozzle may include, for example, but are not limited to the means of heating the chamber. The nozzle may also be passively temperature controlled through thermal conduction from the heating chamber.

Upon cooling, the PCL or similar material will again recrystallize and return to its original (i.e., prior to heating) crystalline state. The methods of measuring crystallinity in PCL are disclosed by M. J. Jenkins, "The effect of molecular weight on the crystallization kinetics of polycaprolactone", Polymers for Advanced Technologies, 2006; 17:474-478. A surprising feature of this property that makes it distinct from the properties of a thermoset material (e.g., PMMA) or a hardening ceramic is that the material can be returned to the pliable, flowable phase if desired. For instance, if during implantation the material prematurely hardens or if the surgeon is not content with the placement of the material or the hardware within it, it can be reheated and remanipulated. Any heating device could be used for this reheating including the Synthes in Situ Bender/Cutter Kit (P/N 530.521) or the nozzle itself. Also, molten material can be applied to material that has already cooled. The molten material advantageously will reheat the interface between the molten material and the cooled material and the materials will bond. In one embodiment, PMMA and CaP cement do not bond at the interface and additional material cannot be added. Therefore, these latter materials do not provide the same flexibility for fine tuning the implantation.

In some embodiments, the material will not recrystallize immediately upon cooling to a temperature below Tm. In such embodiments, the material remains pliable and flowable for a period of time despite the temperature being below Tm. This allows the user to handle and work with the material at temperature below Tm with bare hands without burning. In one embodiment, this allows for implantation and manipulation of the material into a tissue without a risk of necrosis.

It has further been found in simulated injection models at body temperatures, that material that has been heated to 80° C. will immediately cool to a temperature of less than about 50° C. upon contact with the bone, yet the material remains flowable. This feature advantageously allows for implantation without the risk of thermal necrosis. PMMA on the other hand remains exothermic for an extended period of time and can achieve temperatures in excess of about 90° C. Due to this delay of recrystallization, it is possible to utilize higher melting point materials than previously disclosed in U.S. Pat. No. 6,290,982 while still retaining clinically acceptable results.

All molecular weights of PCL will generally melt at 60° C. However, the viscosity of the material above the melt point is significantly affected. The use of low melt polymers for injection has focused on relatively low Mw aliphatic polyesters. For example, U.S. Pat. No. 6,290,982 discloses Mw of less than 10,000 where the material hardens into a wax, not a structural solid; U.S. Pat. No. 4,645,503 discloses polymers in the range of 400-5000 Mw; and U.S. Pat. No. 5,679,723 discloses injecting a material with an I.V. of between 0.05 and 0.5, the disclosure of each U.S. Patent is hereby incorporated by reference in its entirety.

The PCL of the present invention can be readily blended with a variety of materials through standard methods including melt or solvent blending. In one embodiment, melt blends are made with barium sulfate, strontium carbonate and β-TCP. In one example, blending at a β-TCP to powder ratio of 70/30, 85/15, 92.5/7.5 was used. In another example, blends having a ratio of β-TCP to barium sulfate of 99/1, 99.5/0.5 were used. In one embodiment, solvent blending was used to produce PCL/β-TCP blends at a ratio of 60/40. In one embodiment, blends are useful by allowing better visualization through X-ray during surgery. In one embodiment, the blend with β-TCP is useful since a β-TCP blend has a composition similar to that of bone. In one embodiment, another osteoconductive phase of calcium is used (e.g., hydroxyapatite).

In a preferred embodiment, a radiopacifier is combined with the PCL of the present invention. The radiopacifier provides several advantages, such as enabling the PCL to be visualized by a surgeon during and after implantation. Fluoroscopic visualization is especially important when the material is injected in areas without direct visualization such as, for example, a screw hole or a vertebral body, to ensure that the placement of the material is appropriate. Examples of radiopacifiers useful with the present invention include calcium compounds, barium sulfate, strontium carbonate, zirconium compounds, magnesium compounds, titanium oxides and compounds, combinations thereof, and the like. In general, any element or compound with a radiodensity greater than the radiodensity of the polymer matrix could be used.

Figure 10:
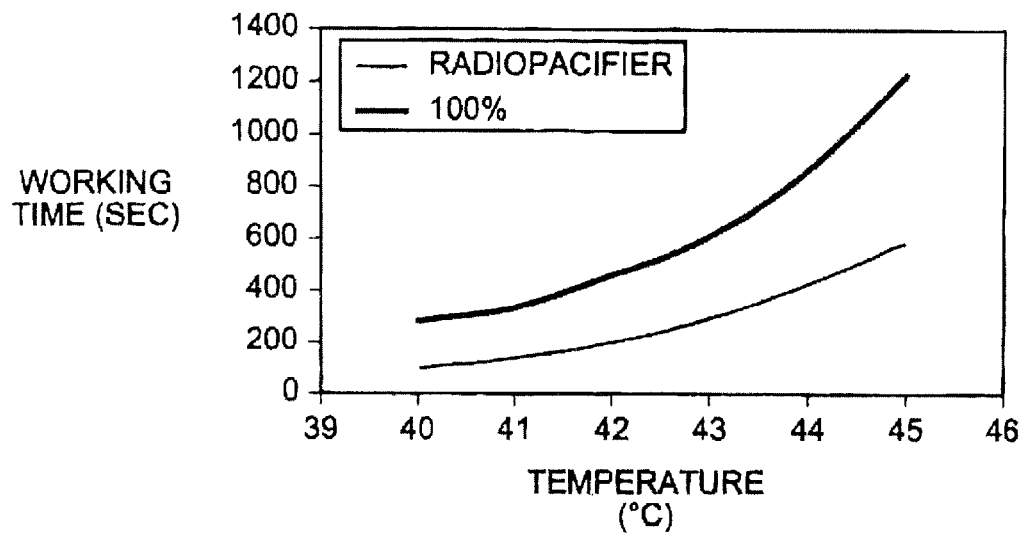
FIG. 10 is a graph showing one embodiment of a rate of recrystallization of PCL with the addition of a radiopacifier.

Another surprising result of combining a radiopacifier with the PCL of the present invention is the formation of nucleation sites within the PCL during hardening of the PCL. In one embodiment, as PCL cools and begins to crystallize, the crystallization first takes place in the areas of discontinuity. Radiopacifiers increase the degree of discontinuity in the polymer structure. In one embodiment, adding the radiopacifiers increases the number of nucleation sites which allows for faster crystallization (e.g., setting) time. This allows for the adjustment of the working time of the polymer. FIG. 10 shows the increase in the rate of recrystallization with the addition of a radiopacifier. The effect of faster recrystallization is evident with the addition of as little radiopacifier as approximately 0.5% by weight.

In one embodiment, adding radiopacifiers will decrease the tensile strength after hardening.

Other materials that can be blended with PCL include calcium materials in the form of powders and granules. In a preferred embodiment, β-TCP such as the Synthes commercial product chronOS™ is combined with the PCL of the present invention. Small amounts (e.g., up to about 5% by weight) of fine β-TCP particles may be added to the PCL to provide radiopacity and enhanced osteoconductivity of the surface. In one embodiment, the fine particles have a particle size range of 1 μm to 50 μm. In one example, the fine particles of β-TCP used are available from Fluka. However, large amounts (e.g., about 10% by weight or greater) of β-TCP granules in the order of between about 0.5 to about 2.8 mm diameters can also be added to PCL at ratios of up to 80% or more by weight. In some embodiments, the blended material may no longer be readily injectable, but can still be manipulated as putty when heated above the melting temperature (Tm) and becomes rigid when fully recrystallized.

In some embodiments, by utilizing a high molecular weight PCL and selecting relatively large granules (e.g. about 1.4 mm to about 2.8 mm), it is possible to prevent encapsulation (e.g., PCL in the melt phase completely covering the β-TCP particle and thus preventing the β-TCP from coming into direct contact with cells) of the calcium phase. For example, in embodiments where an interconnectivity of the calcium phase is maintained, the body will be able to remodel the material in vivo through the process of creeping substitution independent of the resorption rate of the polymer. Therefore, bony ingrowth can be obtained. In one embodiment, the interconnectivity is maintained by at least a portion of the β-TCP particles interspersed within the PCL are in contact with one another (i.e., not encapsulated). Because the β-TCP particles are porous, an interconnected porous structure is created throughout the implant resulting in penetration of cells and other materials into the implant, leading to resorption and creation of new bone. It also provides for a degree of interconnected porosity that can benefit the maintenance of vascularity to the surrounding bone and tissue.

Additional compounds could be added to the PCL or composite phase including, but not limited to, antibiotics, growth factors, peptides, proteins, small molecules, biphosphanates, hormones, parathyroid hormone (PTH), anti-inflammatories, chemotherapeutics, antiseptics, demineralized bone, autologous bone, bone marrow aspirate, blood, platelets, platelet-rich plasma, cells, stem cells, osteoprogenitor cells, combinations thereof, and the like. These additional compounds can be used to stimulate bone growth, maintain or increase bone mineral density, increase the rate of fracture healing, reduce tumor size, reduce pain or inflammation, treat infection, prevent infection, combinations thereof, and the like.

In some embodiments, thermoplastic materials (e.g., such as but not limited to PCL) reduce encapsulation of a second composite phase. As discussed above, thermoplastic materials of a preferred embodiment have an increased viscosity over existing bone augmentation materials due to the higher molecular weight, therefore the polymer phase has less of a tendency to spread out and cover adjacent composite particles. In one embodiment, the polymer phase is more cohesive and tends to hold to itself rather than flow and spread. In one example, thermoplastics having a molecular weight range of 50,000 to 150,000 have an rheological properties that to promote such cohesiveness.

In some embodiments, the materials of the present invention provide improved control of the materials during injection. The prior art taught the benefit of using a lower Mw material for improved flow during injection, however, lower Mw materials provide less control of the material during injection than materials of higher Mw. In some embodiments, the use of high Mw material actually provides increased control over the direction of injection. The polymer will tend to flow in the direction of injection and will have less of a tendency to backflow. This is especially advantageous when trying to apply the material to cancellous bone that is adjacent to an intramedullary canal, area devoid of cancellous bone such as the proximal humerus or areas of high vascularity such as vertebral bodies. Low viscosity materials tend to find the path of least resistance and flow into these areas preferentially. A higher viscosity material, such as the material of the present invention can flow in the direction of injection, rather than back-flowing, and will form a bolus of material.

In some embodiments, the materials of the present invention reduce extravasation during implantation. The material according to the present invention has a lower tendency to extravasate and flow into joints, soft tissue, vascular system, etc than the materials of the prior art. The cohesive nature of high Mw polymers makes them prefer to adhere to themselves, thus creating an expanding bolus of material. The prior art materials including PMMA, CaP cements, and lower Mw thermoplastics have more of a tendency to creep in between fragments and into joint spaces or can become completed separated from the flow creating a particle that can lead to an embolitic event such as a pulmonary embolism. Such events can occur, for example, during vertebroplasty procedures using PMMA cement. The material of the present invention is also polymerized (unlike PMMA in its injectable state) so that the polymer chains that provide this improved cohesiveness are fully developed. Also, use of a fully polymerized material reduces or eliminates the risk associated with free monomers, such as toxicity risks.

In addition to the higher Mw, the crystalline nature of the material is beneficial for the prevention of extravasation. In one embodiment, the outer most regions of the injected bolus will have increased viscosity as it becomes crystalline and form a skin. This outer skin, while still pliable, will not allow for significant flow. In some embodiments, the skin forms a containment barrier. Prior art bone augmentation materials do not have such a property. In some embodiments, the formation of skin is particularly useful to improve kyphoplasty, distal radius and proximal tibia procedures and any other procedure where the extravasation of material may have deleterious effects including but limited to entering joint spaces, becoming vascularized or becoming entrained into bony fragments. In one embodiment, it is necessary for the outer skin to only partially crystallize in order to form the beneficial effects as described herein. For example, in one embodiment, when as little as about 5% to about 10% of the original crystallinity of material is achieved the material forms an outer skin that is useful for achieving the objective of the present invention including embodiments for preventing extravasation during the placement of thermoplastic material into tissue.

Other methods of containment of injectable materials such as disclosed in US Patent Appl. Pub. No. 2005/0209629, incorporated herein in its entirety, have required the introduction of a separate containment device. In one embodiment of the present invention, a separate containment device is not needed to contain the injected materials. In one embodiment, the injected material becomes its own containment device.

In other embodiments, the material of the present invention provides improved shape retention during handling and before recrystallization over prior art bone augmentation materials. In some embodiment, the use of PCL/β-TCP putty allows for the final shape of an implant to be controlled. For example, in one embodiment, the final shape of the implant matches the shape of the void in the tissue.

In one embodiment, the materials of the present invention, having a high Mw, have an increased viscosity before recrystallization. Therefore, the material holds the shape in which the material is applied or manipulated into. This shape may include the shape of the void created during orthopedic trauma, a cavity that is surgically created or the desire shape for augmentation of osteosynthesis hardware. For example, where material is applied in areas without adjacent support, such as a bolus of material attached to subchondral bone distally, but otherwise surrounded by body fluids, the high molecular weight material would hold its shape where lower molecular weight material would not. One advantage to the shape-holding effect is the ability of a screw or other hardware or fastening device to gain sufficient purchase when inserted into the molten bolus.

In some embodiments, the material of the present invention includes the ability to reduce fractures and compress cancellous bone. Due to the viscous nature of the material, it can be used to move mobile bone fragments and even compress low density cancellous bone either during injection or if moved with digital pressure or with a bone tamp. Lower viscosity materials will tend to flow away and will not transfer the force.

In some embodiments, the material of the present invention includes the ability to perfuse into cancellous bone and/or displace marrow. The displacement of bone marrow is optimized when the viscosity of the injected material is substantially greater than the viscosity of the marrow. The viscosity of marrow is highly variable and is temperature and shear rate dependent. In one study, marrow has been measured at 37.5 cP at body temperature. Without being limited the measurements of this study, in one embodiment of the present invention, viscosity of the injected material is substantially greater than 37.5 cP. Due to the perfusability of the material being injected in a fully polymerized state and due to the relatively high molecular weight and high inherent viscosity of the material, the material will tend to displace marrow when flowing through a cancellous structure. Another advantage to using polymerized material is that it will not phase separate during this application. CaP cements do not inherently have this ability and will tend to phase separate if pressurized into cancellous bone with marrow. Even PMMA when initially mixed is not of sufficient viscosity to displace marrow and will tend to channel and find paths of least resistance. It is not until it becomes more polymerized that PMMA will displace the marrow rather than flow around it, however, the window of time when working with PMMA is very limited as the material becomes fixed and is no longer movable.

Additionally, PCL has a superior cohesiveness compared to existing cements. Thus the material of the present invention rebonds to itself, even in the presence of an aqueous solution. Further, it will not be dispersed by any known bodily fluid. According to some embodiments, implanting or injecting the material of the present invention through cancellous bone will divide the material and reincorporate the material many time as it passes over the trabecullae. Therefore, the ability of the material to rebond to itself and not disperse is of great importance whenever a cancellous bone structure is augmented with a material such as in vertebral body augmentation and osteosynthesis hardware augmentation. PMMA does not have the same level of cohesiveness in an aqueous environment and CaP cements have a tendency to become disperse in bodily fluids which affects the strength of the final set product.

In other embodiments, an especially important aspect of the present invention is that the properties of the injected material can be manipulated by varying flow rates and controlling temperature within the injected mass. In one embodiment, a hole or other access means can be drilled into a bone such as a vertebral body, tibial plateau, distal radius, proximal femur or other metaphyseal bone region and the material can be injected into this space utilizing, for example, a heated inject gun as described previously. The flow of material can be stopped temporarily after the void is filled and the mass of material is interdigitated into the surround bone. The polymer can be treated to at least partially recrystallize by cooling it to below the Tm. This treatment can either be active cooling or passive heat dissipation. In one embodiment, the treatment of the bolus includes simply allowing the bolus to cool. After the material has become at least partially crystalline, additional material can then be injected under pressure. The material that was initially injected now is at semi-solid state and is expanded by the warmer, less crystalline material of the second inject phase. This semi-solid outer skin contains the inner, more flowable material and a force can be generated that can be used to compress cancellous bone, reduce mobile bone fragments, or increase the height of a collapsed vertebral body. The entire mass of material can then cool to physiological temperature and become fully crystalline and the reduction is permanently maintained. In one embodiment, partially crystalline skin is used to reduce extravasation of the injected material by producing a containment skin as disclosed above.

In one embodiment, this procedure has an advantage over known kyphoplasty procedures that require a specialized balloon to be inflated for the reduction and wherein the balloon is removed and a hardenable biomaterial such as PMMA is then injected. In one embodiment of the present invention, there is the advantage of performing both operations in one inject step which prevent loss of reduction, for example, when the balloon is removed. Also, extravasation of the final injected material is minimized since it is contained by the semi-solid outer skin or shell.

Figure 11:
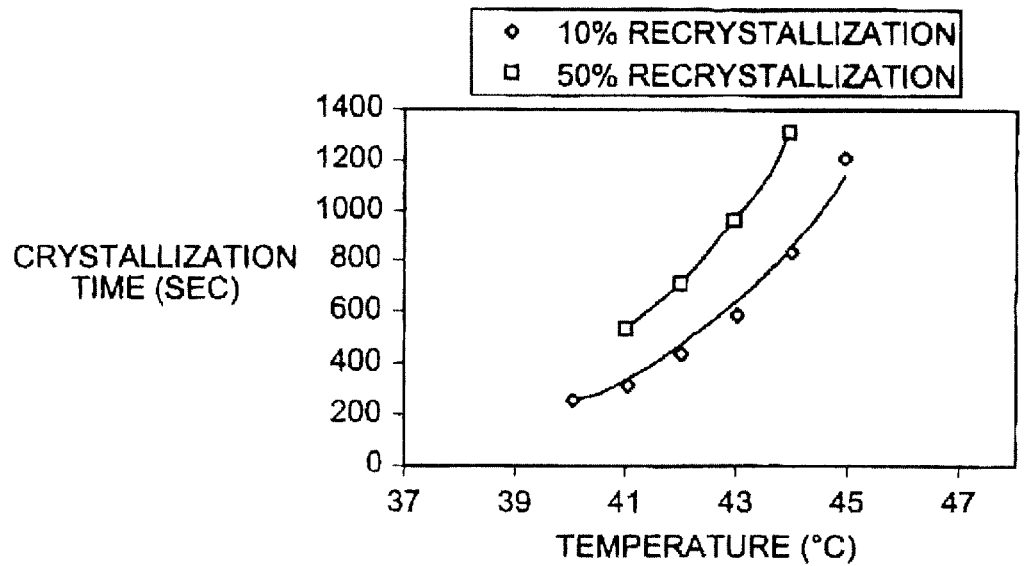
FIG. 11 is a graph illustrating one embodiment of recrystallization time of 100% PCL as a function of temperature.

In some embodiments, the flow rates and temperatures of the materials of the present invention are adjusted to control the rate of recrystallization. FIG. 11 illustrates the relationship between temperature and the time for the material to recrystallize 10% and 50%.

As disclosed above, the materials original properties can be substantially achieve when approximately 10% of the original crystallinity is developed. This time for recrystallization can be approximately 20 minutes at 45° C. and approximately 4.5 minutes at 40° C. Thus the material can be controlled to a temperature between physiological temperature and the melt temperature to yield a range of working times for the surgeon during the implantation period. In one embodiment the temperature is controlled to exit the nozzle just above physiological temperatures or even room temperature to promote rapid recrystallization of the material. In other embodiments, the material is controlled to a temperature well above physiological temperature to extend working time. The temperature of the material, in some embodiments, is controlled by varying the rate at which it is expelled from the system, passive heat loss as it travels through the nozzle, active cooling or heating in the nozzle, temperature in the material holding chamber, and/or active or passive temperature control in the injected bolus. The desired temperature range is generally between approximately 37° C. and approximately 60° C. In some embodiments, temperature is controlled to a range of from approximately 0° C. to approximately 150° C. in certain cases.

In some embodiments, the initial void or drill hole is reduced in temperature so that the initial injected material crystallizes more readily. In another embodiment, the initial hole is heated to retard crystallization and increase the workable time of the materials. In some embodiments, this change in temperature is generated, for example, by a heating or cooling probe or by irrigating with a solution of the appropriate temperature.

In other embodiments, the initial injected material is treated by cooling the material with an inserted probe. This would create a hollow annulus for further injection of material and cools the skin to promote crystal formation.

In further embodiments, the injection cannula, needle, or auxiliary instrument is used to selectively cool and/or heat various regions of either the initial injection or subsequent injections of materials. For instance, in the case of a vertebroplasty, the anterior and posterior portions of the injected bolus could be cooled to promote crystallization in these regions. Thus upon further injection of material, the flow and expansion would be preferential to the radial direction; thus allowing for a more controlled bony reduction with less extravasation risk in undesirable areas such as towards the spinal cord.

An additional feature of one embodiment of PCL material of the present invention is that it has a modulus (i.e. stiffness) that is similar to healthy cancellous bone, as illustrated below in Table 1. It also has significant strength in both compression and tension and excellent elongation. This combination of materials properties is unique and ideally suited for the clinical application. The mechanical properties allow drilling and screwing of the material without cracking. The high elongation means that the material will yield with a ductile failure rather that cracking with a catastrophic failure. In some embodiments, the PCL material of the present invention has advantages over Calcium Phosphate (CaP) that is especially prone to cracking and over PMMA that is a relatively brittle plastic and does not have the same inherent ductility.

TABLE 1

| Material | Approximate Modulus (MPa) |
| --- | --- |
| Cancellous Bone | 250 |
| PCL | 250 |
| PMMA | 3000 |
| CaP Cement | 3000 |

There are many benefits of matching the modulus of cancellous bone. A filling or augmentation material that is stiffer than the surrounding bone creates a construct that is more rigid than the pre-trauma condition. It has been speculated in vertebroplasty procedures, for instance, that this sudden and significant increase in stiffness of the vertebral body can lead to an increase in the collapse of adjacent levels. The benefit of matching the modulus for hardware augmentation has not been previously disclosed to the inventor's knowledge, but can be illustrated by the following example:

As the above results illustrate, augmentation with PCL around a screw can reduce the stress at the bone interface by 56.50%. This is expected with any form of augmentation since there is greater surface area. What is more surprising is that there is 34.07% less maximum stress when using PCL vs. PMMA. In this case both scenarios have the same interface surface area, but the lower modulus of the PCL allows the forces to be transferred over a larger area due to internal deformation of the material.

In one embodiment, an even lower modulus material (i.e. elastomer) may yield even lower stress at the interface due to even more internal deformation. However, there is a critical point where it is not failure at the bone interface, but rather the screw pulls out of the augmentation material. In some embodiments, where screw designs have been optimized for performance in normal cancellous bone, matching the properties of that bone should result in ideal screw/material interface.

According to some embodiments, potential clinical applications of the PCL material and composites include fracture fixation in the head of a proximal humerus. The proximal humerus is an especially challenging fracture in osteoporotic bone because the center resorbs and only subchondral bone remains. It is very difficult for screws to gain sufficient purchase in the thin shell of subchondral bone. Therefore, in one embodiment, the material of the present invention is tested as a fixation method for the proximal humerus. According to one example, PCL material of the present invention was injected into the cancellous bone to interdigitate with it. Screws were then placed into the semi-molten material and the construct was allowed to cool completely. The screws were not actually in the bone, but rather the PCL was used as a bridging material between the bone and the screws. Since the PCL interdigitates, it forms a mechanical bond to the cancellous bone that exceeds the strength of the bone. The PCL material is also drillable with standard orthopedic drills and can be redrilled when it has recrystallized. In one embodiment, a self-drilling screw is placed directly into the material. Thus in one embodiment, the material is allowed to cool and the bolus is drilled and the screw is then placed. Testing has shown that the resistance to screw pull out is increased approximately 35% in this embodiment vs. placing the screw in a molten bolus. Previous materials for hardware augmentation such as PMMA do not readily drill and leave non-resorbable debris making redrilling impractical. CaP cements are easily drilled, but often fracture during the drilling and screwing process due to their brittle nature.

According to another embodiment, the rheological properties of the PCL material can be manipulated by exposing the materials to radiation. Exposure of the material to gamma irradiation in the range of approximately 20 kGy to approximately 40 kGy induces a shape memory effect on the polymer. When the material is heated to a temperature greater than Tm and allowed to cool, the material will therefore have a tendency to return to the shape it was when irradiated. This shape memory effect thus provides a degree of 'spring back' to the material. This 'spring back' is due to a crosslinking effect of the irradiation and has two distinct advantages. First, the spring back helps reduce or prevent extravasation of the material when the flow of the material has ceased and the most remote regions of the material will be pulled towards the center of the bolus of the material rather than continuing to flow outward. The second advantage is that the spring back can cause the material to tighten around an implant, such as the threads of a screw inserted into a molten mass of the material, thereby enhancing the mechanical interface of the material.

In one preferred method, the PCL is exposed to gamma irradiation before heat melting. In one embodiment, this radiation crosslinking effect is controlled by the level of irradiation. In one embodiment, the source of radiation is any high energy radiation source such as gamma irradiation or electron beam irradiation. While there is no theoretical minimum or maximum radiation level that can be used, high levels of irradiation above 50 kGy are known to degrade polymers and may not be practical. In one embodiment, gamma radiation at levels of about 15 kGy to about 50 kGy are used. In one embodiment, the inherent viscosity of PCL is not greatly affected by the time that PCL is exposed to such radiation. After being placed in simulated physiological conditions, mechanical testing of irradiated PCL has been performed and that testing illustrates that in the first six months after such irradiation, there is an insignificant effect on the mechanical properties of the PCL in comparison to PCL that is not irradiated. The mechanical properties continue to be similar after a period of one year.

Thus, in one embodiment there is a method fracture reduction in a tissue that includes exposing to gamma radiation a mass of polycaprolactone characterized by a first shape; heating the mass of irradiated polycaprolactone to a temperature above its melting temperature; introducing the heated mass of polycaprolactone into a tissue annulus in a shape deformed from the first shape; and allowing the material to return to a shape that approaches the first shape. In one embodiment, the mass of polycaprolactone is exposed to gamma radiation in a cartridge that is insertable in an injection device. In one embodiment, the deformed state is achieved when the material is discharge from the injection device (e.g., through a needle). In a further embodiment, the material returns to a shape that is very close the original shape (e.g., when it cools). In one embodiment, the material is prevented from returning to original shape because it fills the void of a tissue before it reaches its original shape (e.g., when it cools). In another embodiment, the material substantially reaches its original shape (e.g., when it cools).

Figure 1:
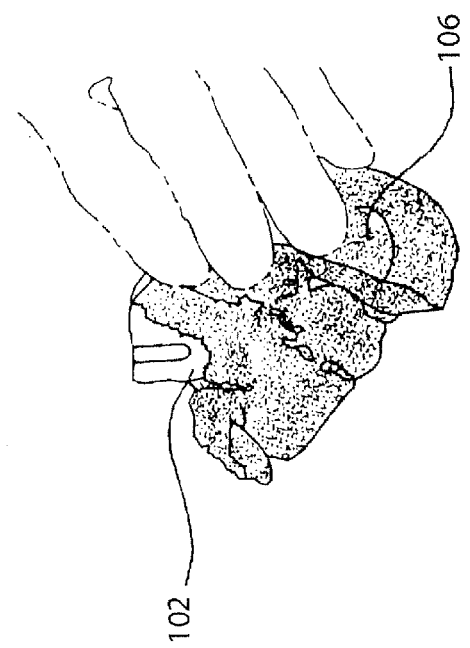

Referring to FIGS. 1 and 2, a PCL material 102 was injected into a 4.2 mm drill hole of a cadaver bone 106 before placement of a 5 mm locking screw 114. In some embodiments, a material 102 may include a shape-holding effect such that the material 102 supports a screw 114 or other hardware. In some embodiments, the material 102 is injected in a flowable state, such as a molten state. In some embodiments, the material 102 is exposed to a temperature change to achieve a second condition which includes an at least partially crystalline skin. In certain embodiments, the second condition is a semi-solid state.

Figure 3:
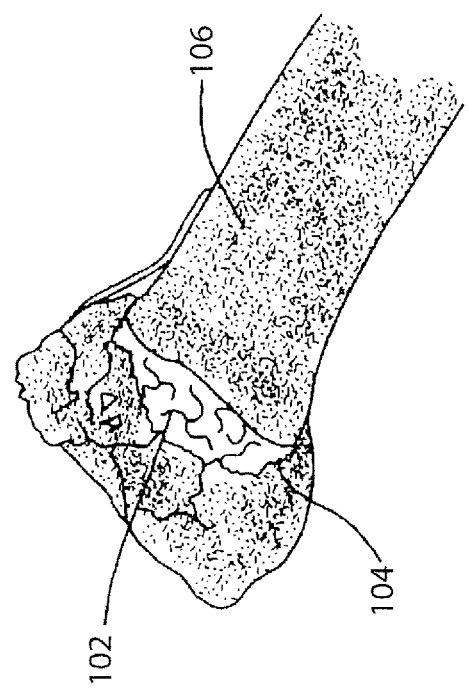
FIG. 3 shows an application of the PCL used to fill a bone void and to act as a reduction tool according to an embodiment of the present invention.

Referring to FIG. 3, an application of PCL material 102 was used to fill a bone void 104 and to act as a reduction tool. According to some embodiments, the material 102 is heated in a water bath and applied with digital pressure. In some embodiments, the material 102 holds a shape in which the material 102 is applied or manipulated into. The shape may include, for example, the shape of a void 104 in a tissue. In some embodiments, gamma radiation may be used to induce a shape memory characteristic on a material.

Figure 4:
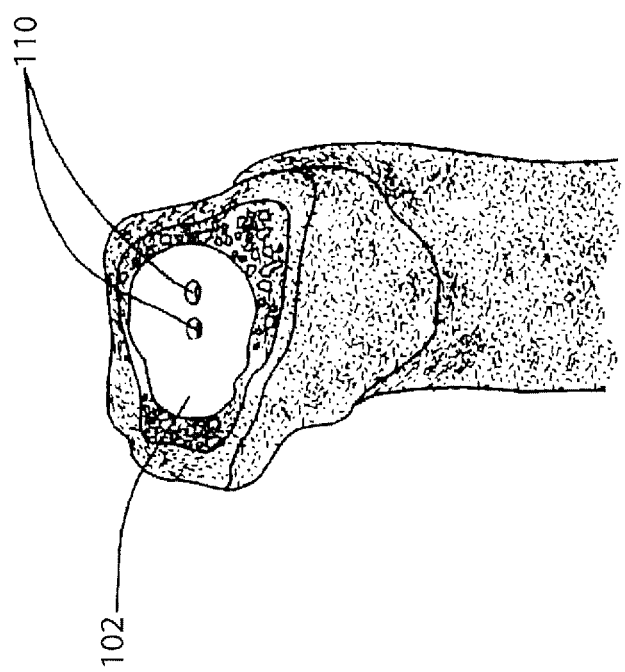
FIG. 4 shows a proximal femur depression filled with PCL material according to an embodiment of the present invention.

Referring to FIG. 4, a proximal tibia depression was filled with PCL material 102. In some embodiments, the material 102 is heated before insertion. In some embodiments, the material 102 is heated in a water bath. Upon cooling, the material 102 may be drilled to create holes 110. In some embodiments, a material 102 may be introduced into an annulus defined by the tissue.

Referring to FIG. 5, the material 102 is shown being used to augment a screw 112 in the intramedullary canal 118. In one embodiment, the illustrated placement of the material 102 may provide significantly higher pull out strength since the forces will be distributed over a broader area of the endocortex. In some embodiments, the material 102 may include a shape-holding effect such that the material may support a screw 112 or other hardware even when the material 102 is surrounded by body fluids.

Figure 7:
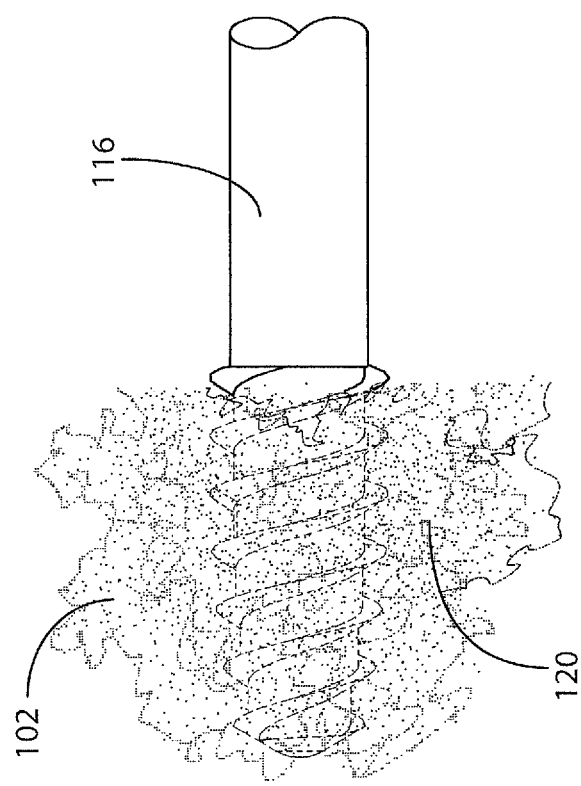

Referring to FIGS. 6 and 7, the material 102 may provide augmentation of a DHS screw 116. In FIGS. 6 and 7, an 8 mm hole was drilled in simulated cancellous bone 120. A bolus of material 102 was inserted into the hole and a DHS screw 116 was driven into the material 102. The PCL material 102 flowed into the simulated cancellous bone 120. The material 102 provided increased holding power and the ultimate failure was at the PCL 102/bone 120 interface. In some embodiments, the material 102 may form an at least partially crystalline skin which may displace at least a portion of the tissue. In some embodiments, cancellous bone may be compressed when force is exerted upon it. In some embodiments, the at least partially crystalline skin may prevent extravasation of the PCL material 102.

Figure 8:
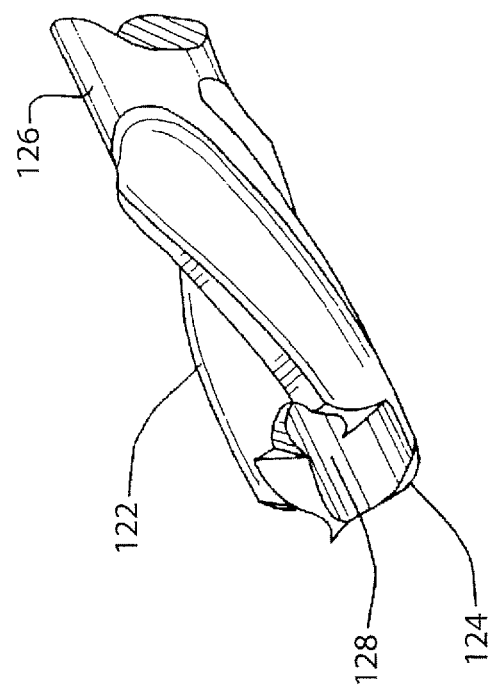
FIGS. 8 and 9 show a spiral nail blade modified to inject PCL material and to allow the material to flow preferentially in one direction.
Figure 9:
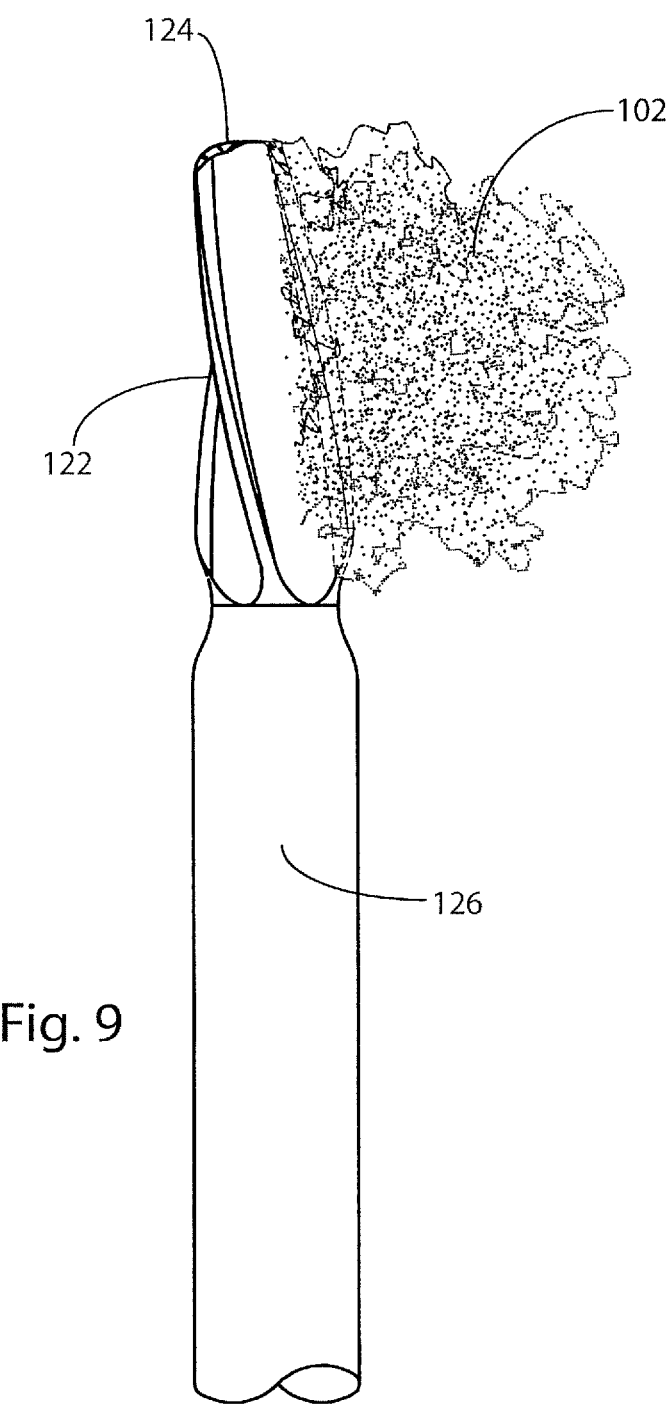

Referring to FIGS. 8 and 9, one embodiment of the present invention relates to a modified nail including a channel to deliver PCL material 102. A spiral blade 122 of a TFN Nail 126 (Synthes, USA) used for proximal femur fractures has been modified by removing material at the most distal end 124. The nail 126 may be inserted into a proximal femur according to the standard procedure. A heated cartridge of PCL may be attached to the proximal end of the blade 122 and the material 102 may be injected under pressure to allow the material 102 to flow down the cannulation 128 and out of the most distal end 124. The modification to the distal end 124 allows the material 102 to flow preferentially in one direction, in this case the superior direction.

In one embodiment, the material is allowed to cool or is actively cooled after it flows from cannulation 128. In one embodiment, the material is allowed to return at least partially to an original shape after it is allowed to cool. In one embodiment, the original shape is a substantially tubular shape. In one example, the material has an original shape that corresponds to the shape and diameter of a mold cavity in which the material was exposed to gamma radiation to induce a shape memory effect.

Figure 12:
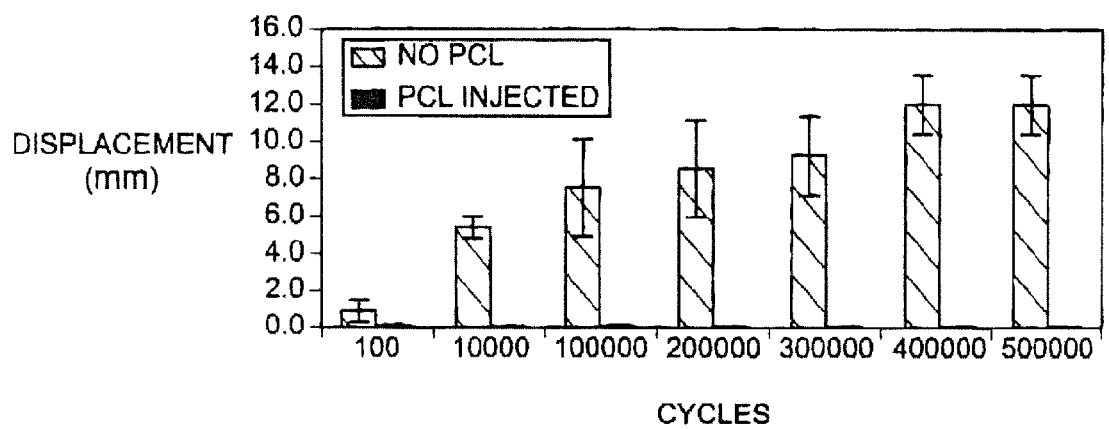
FIG. 12 is a graph illustrating head displacement vs. stress cycles at 1.2 kN with TFN blade in Sawbones Foam 12.5 pcf density.

Cyclic compression testing was done on the construct and compared to the same conditions without the use of PCL 102. FIG. 12 shows a graph of head displacement vs. stress cycles of a TFN nail in Sawbones Foam 12.5 pcf density with or without PCL at a load of 1.2 kN. As FIG. 12 illustrates, there is significantly less head displacement even over cyclic loading over 500,000 cycles at a load of 1.2 kN.

In order that the invention may be understood, preferred embodiments which are given by way of example only, are described with reference to the appended drawings. Accordingly, the preferred embodiments are described for convenience of reference and without limitation of the invention to embodiments described. The scope of the invention being defined by the claims appended hereto.

EXAMPLES

Example 1

PCL Composite Composition

A PCL/β-TCP composite was produced with the following composition:
PCL component: Sigma PCL 440744, I.V. 1.59, 20% by weight
β-TCP component: chronOS granules, 1.4-2.8 mm
The above components were heated to above 60° C. and kneaded by hand and allowed to cool. A structurally sound, cohesive mass was formed. The composite was reheated and manipulated to simulate manipulation by the surgeon and formed into a ball. It was again allowed to cool.

The composite material was placed in a solution with Alizarin red S (a red dye selective for calcium). Areas that still had exposed calcium were dyed red and areas encapsulated by polymer were yellow. A significant amount of calcium was free from encapsulation. The same composite was sectioned and the dye had penetrated significant portions of the internal structure demonstrating an interconnected porosity.

Example 2

PCL material was injected into a 4.2 mm drill hole in a cadaver and a 5 mm locking screw was placed therein. The material was injected through an injection device as described above and was used for injection set at 80° C. Good perfusion into the relatively dense cancellous bone can be seen in FIGS. 1 and 2.

Example 3

Figure 13:
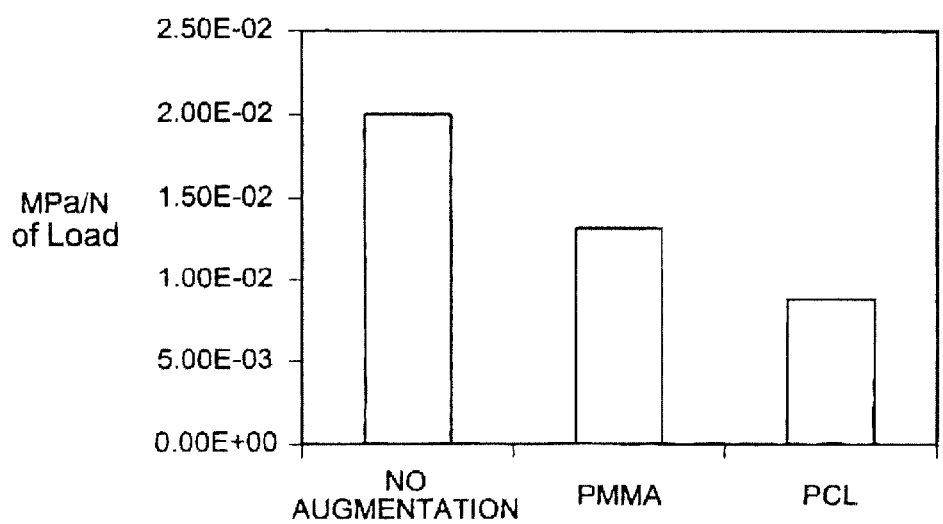
FIG. 13 is a graph showing exemplary maximum stress at bone interface.

A finite element analysis (FEA) was performed on a construct simulating a stainless steel screw in cancellous bone with an offset load. The modulus of each of the materials was assigned as reported in Table 1, above. Three conditions were tested in the FEA simulation:
1) Ø8 mm stainless steel screw in cancellous bone block without augmentation
2) 3 mm of PMMA augmentation around screw
3) 3 mm of PCL augmentation around screw
The screw was rigidly constrained on the proximal end and a unit load was placed on the cancellous bone at the distal end. The maximum stress at the screw to bone interface was assessed with the results shown in FIG. 13.

While the detailed description represents preferred embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, sizes, and with other elements, materials, and components, without departing from the spirit or essential characteristics thereof. One skilled in the art will appreciate that the invention may be used with many modifications of structure, arrangement, proportions, sizes, materials, and components used in the practice of the invention, which are particularly adapted to specific needs and operating requirements, without departing from the principles of the present invention. The presently disclosed embodiments are therefore to be considered in all respects as illustrative and not restrictive, the scope of the invention being defined by the appended claims, and not limited to the foregoing description or embodiments.

We claim:
1. A method of hardware fixation for the treatment of a bone fracture, comprising:
    irradiating a polycaprolactone composition to induce a shape memory property;
    heating the polycaprolactone composition having a first shape to above its melting point to achieve a second shape deformed from the first shape, wherein the modified composition is a polycaprolactone mixed with a radiopacifier,
    injecting the modified composition in its second shape through a cannulated device into a bone site;
    applying a fixation device to the bone site such that the fixation device contacts the modified composition in its second shape;
    cooling the modified composition below its melting point such that the composition recrystallizes and transitions from the second shape to a shape that approximates the first shape, wherein the recrystallized modified composition supports the fixation device.
2. The method of claim 1, wherein the step of applying the fixation device occurs before the step of injecting the modified composition.
3. The method of claim 2, wherein the cannulated device is the fixation device.
4. The method of claim 1, wherein the step of applying the fixation device occurs after the step of injecting the modified composition.
5. The method of claim 1, further comprising actively altering the temperature of the modified composition in the second shape.
6. The method of claim 5, wherein the step of actively altering is actively heating.
7. The method of claim 5, wherein the step of actively altering is actively cooling.

* * * * *